US010866201B2

(12) United States Patent
Best

(10) Patent No.: US 10,866,201 B2
(45) Date of Patent: Dec. 15, 2020

(54) LUBRICANT DEBRIS MONITORING SYSTEM FOR GAS TURBINE ENGINE

(71) Applicant: PRATT & WHITNEY CANADA CORP., Longueuil (CA)

(72) Inventor: Alexander Best, Beaconsfiled (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 465 days.

(21) Appl. No.: 15/825,990

(22) Filed: Nov. 29, 2017

(65) Prior Publication Data
US 2019/0162687 A1    May 30, 2019

(51) Int. Cl.
| | |
|---|---|
| G01N 27/04 | (2006.01) |
| F02C 7/06 | (2006.01) |
| G01N 33/28 | (2006.01) |
| F01D 21/00 | (2006.01) |
| F02C 7/00 | (2006.01) |
| F02C 3/04 | (2006.01) |

(52) U.S. Cl.
CPC ......... G01N 27/045 (2013.01); F01D 21/003 (2013.01); F02C 7/00 (2013.01); F02C 7/06 (2013.01); G01N 33/2888 (2013.01); F02C 3/04 (2013.01); F05D 2220/32 (2013.01); F05D 2260/607 (2013.01); F05D 2260/98 (2013.01)

(58) Field of Classification Search
CPC .... G01N 27/045; G01N 33/2888; F02C 7/00; F02C 7/06; F02C 3/04; F02D 21/003; F02D 2220/32; F02D 2260/607; F02D 2260/98; H01L 27/16
See application file for complete search history.

(56) References Cited

U.S. PATENT DOCUMENTS

| | | | | |
|---|---|---|---|---|
| 2,462,715 A | * | 2/1949 | Booth | H01F 7/02 200/61.09 |
| 2,878,342 A | * | 3/1959 | Arthur | B03C 1/282 200/61.09 |
| 3,193,815 A | * | 7/1965 | Prestel | G01N 15/0656 340/627 |
| 3,373,352 A | * | 3/1968 | Huigens | G01N 15/0656 324/204 |
| 3,404,337 A | * | 10/1968 | Pool | F16N 29/00 324/439 |
| 3,432,750 A | * | 3/1969 | Botstiber | G01N 27/74 324/439 |
| 3,553,672 A | * | 1/1971 | Smith | G01N 15/0656 340/627 |

(Continued)

*Primary Examiner* — David J Bolduc
(74) *Attorney, Agent, or Firm* — Norton Rose Fulbright Canada LLP

(57) ABSTRACT

There is disclosed a lubricant debris monitoring system for a gas turbine engine. The system includes a magnetic chip collector having electrodes defining a gap therebetween configured to be filled with lubricant. The magnetic chip collector generates a magnetic field for attracting the debris. The system further includes a processor configured to be connected to a power source and for performing an analysis of an signal between the electrodes. The processor stores occurrences of at least one characteristic of the signal exceeding a respective threshold. The system further has a communication system communicatively connected to the processor and configured for transmitting the analysis of the signal.

19 Claims, 3 Drawing Sheets

(56) References Cited

U.S. PATENT DOCUMENTS

| | | | | |
|---|---|---|---|---|
| 4,008,464 A * | 2/1977 | Hobbie | | B60R 16/0232 340/631 |
| 4,070,660 A * | 1/1978 | Tauber | | G01N 33/2858 340/631 |
| 4,100,491 A * | 7/1978 | Newman, Jr. | | G01V 3/08 200/61.09 |
| 4,323,843 A * | 4/1982 | Batham | | F01M 11/10 200/61.09 |
| 4,345,202 A * | 8/1982 | Nagy | | G01N 22/00 324/632 |
| 4,686,857 A * | 8/1987 | Kato | | G01N 33/2888 324/698 |
| 4,731,578 A * | 3/1988 | Tsaprazis | | F16N 29/00 324/204 |
| 5,028,318 A * | 7/1991 | Aslin | | B01D 21/02 209/725 |
| 5,061,364 A * | 10/1991 | Metala | | G01N 15/0618 210/85 |
| 5,179,346 A * | 1/1993 | McGee | | G01N 15/0656 324/204 |
| 5,264,832 A * | 11/1993 | Parmer | | G01V 3/02 324/204 |
| 5,406,208 A * | 4/1995 | Bitts | | G01R 31/2836 180/338 |
| 5,708,198 A * | 1/1998 | Fitch | | G01N 15/0656 73/61.42 |
| 5,754,055 A * | 5/1998 | McAdoo | | G01N 22/02 324/553 |
| 5,782,141 A * | 7/1998 | Schoolcraft | | B03C 1/282 74/606 R |
| 6,297,626 B1 * | 10/2001 | Boston | | G01N 15/0656 324/204 |
| 6,392,562 B1 * | 5/2002 | Boston | | G01N 15/0656 324/204 |
| 6,445,177 B1 * | 9/2002 | Higgins | | B03C 1/286 324/204 |
| 6,794,865 B2 * | 9/2004 | Astley | | G01R 33/563 324/306 |
| 7,106,075 B2 * | 9/2006 | Hu | | G01N 33/2858 324/698 |
| 7,581,434 B1 * | 9/2009 | Discenzo | | G01N 33/2888 73/53.01 |
| 8,184,290 B2 * | 5/2012 | Hertens | | G01F 1/667 356/335 |
| 9,006,556 B2 * | 4/2015 | Bell | | F01P 9/06 136/205 |
| 9,205,845 B2 | 12/2015 | Uluyol et al. | | |
| 9,752,956 B2 | 9/2017 | Mckimpson et al. | | |
| 2005/0057267 A1 * | 3/2005 | Nicholson | | G01N 22/00 324/698 |
| 2006/0125487 A1 * | 6/2006 | Itomi | | G01N 33/2888 324/533 |
| 2009/0014245 A1 | 1/2009 | Shevchenko et al. | | |
| 2009/0051350 A1 * | 2/2009 | Becker | | G01N 15/0656 324/204 |
| 2009/0314064 A1 * | 12/2009 | Augros | | B03C 1/286 73/61.42 |
| 2010/0109686 A1 * | 5/2010 | Zhe | | G01M 13/02 324/698 |
| 2011/0315273 A1 * | 12/2011 | Slayter | | F01M 11/04 141/346 |
| 2012/0046896 A1 * | 2/2012 | Flandrois | | G01N 27/10 702/65 |
| 2013/0228647 A1 * | 9/2013 | Bystry, Jr. | | B64D 41/00 244/17.21 |
| 2013/0332045 A1 * | 12/2013 | Uluyol | | B60W 50/00 701/102 |
| 2014/0311240 A1 * | 10/2014 | Fitch | | F01M 11/0408 73/334 |
| 2014/0347032 A1 * | 11/2014 | Reed | | G01V 3/08 324/71.1 |
| 2015/0129361 A1 * | 5/2015 | Hodgkinson | | F16N 29/04 184/6.4 |
| 2015/0280099 A1 * | 10/2015 | Boukai | | H01L 35/22 136/203 |
| 2016/0075438 A1 * | 3/2016 | Akin | | H01L 35/30 307/9.1 |
| 2016/0156285 A1 * | 6/2016 | Elgezabal Gomez | | F01D 5/02 310/306 |
| 2016/0319697 A1 * | 11/2016 | Akin | | F01D 25/24 |
| 2016/0370275 A1 * | 12/2016 | Weiser | | F16N 29/04 |
| 2016/0370341 A1 | 12/2016 | Jean et al. | | |
| 2017/0074157 A1 * | 3/2017 | Mitkari | | H02N 10/00 |
| 2017/0138217 A1 | 5/2017 | Schwarz et al. | | |
| 2017/0248076 A1 * | 8/2017 | Dierksmeier | | F02C 7/185 |
| 2017/0248572 A1 * | 8/2017 | Byington | | F16H 57/0405 |
| 2017/0269036 A1 * | 9/2017 | Foord | | G01N 33/2888 |
| 2018/0030850 A1 * | 2/2018 | Hagen | | F02C 3/04 |
| 2018/0031504 A1 * | 2/2018 | Ricci | | G01N 33/2858 |
| 2018/0187622 A1 * | 7/2018 | Rudolecky | | F01M 11/10 |
| 2018/0364141 A1 * | 12/2018 | Youssef | | G01N 15/02 |

\* cited by examiner

LUBRICANT DEBRIS MONITORING SYSTEM FOR GAS TURBINE ENGINE

TECHNICAL FIELD

The application relates generally to gas turbine engines and, more particularly, to systems and methods used to detect debris within a lubrication system of such engines.

BACKGROUND OF THE ART

Rotating components of gas turbine engines are typically operatively connected to a lubrication system for proper lubrication. With use, the rotating components may wear. Therefore, residue or debris coming from these components may circulate within a lubricant of the lubrication system. Proper operation of the rotating components may be impaired if a concentration, or level, of such debris reaches a given threshold. Moreover, the level of such debris may be indicative of a deterioration of one of the rotating components. Therefore, systems are used to collect said debris. However, many engines and aircraft are only equipped with chip collectors that trap the debris without providing any feedback regarding the level of debris. Periodic maintenance for verifying a state of the chip collector, which are typically very time-consuming, have to be scheduled.

SUMMARY

In one aspect, there is provided a lubricant debris monitoring system for a gas turbine engine, comprising: a magnetic chip collector operatively coupled to a lubrication system, the magnetic chip collector having electrodes defining a gap therebetween, the gap exposed to lubricant of the lubrication system, the magnetic chip collector in use generating a magnetic field for attracting the debris toward the electrodes, the magnetic chip collector configured to generate a signal when a metal chip in the lubricant bridges the gap and allows connection of the electrodes; a processor operatively connected to the electrodes of the magnetic chip collector and connected to a power source, the processor configured for performing an analysis of the signal for detecting occurrences of at least one characteristic of the signal exceeding a respective threshold and for storing the analysis with the occurrences; and a communication system communicatively connected to the processor and configured for transmitting the analysis of the signal.

In another aspect, there is provided a gas turbine engine comprising a lubrication system for lubricating rotating components of the gas turbine engine, the lubrication system having a fluid circuitry operatively connected to the rotating components and configured for circulating a lubricant; the gas turbine engine further having a lubricant debris monitoring system operatively coupled to the lubrication system, the lubricant debris monitoring system having a magnetic chip collector coupled to the lubrication system and having electrodes defining a gap therebetween, the gap exposed to the lubricant, the magnetic chip collector in use generating a magnetic field for attracting the debris toward the electrodes, the magnetic chip collector configured to generate a signal when a metal chip in the lubricant bridges the gap and allows connection of the electrodes; a processor operatively connected to the electrodes and to a power source, the processor configured for performing an analysis of a signal between the electrodes for detecting occurrences of at least one characteristic of the signal exceeding a respective threshold and for storing the analysis with the occurrences; and a communication system communicatively connected to the processor and configured for transmitting the analysis of the signal.

In yet another aspect, there is provided a method of operating a lubricant debris monitoring system of a gas turbine engine, comprising: attracting debris circulating within a lubricant of a lubrication system toward electrodes of a magnetic chip detector, a signal between the electrodes being affected by the debris located within a gap between the electrodes; performing an analysis of the signal between the electrodes to detect occurrences of at least one characteristic of the signal exceeding a respective threshold; storing the analysis with the occurrences; and transmitting the analysis of the signal.

DESCRIPTION OF THE DRAWINGS

Reference is now made to the accompanying figures in which.

DETAILED DESCRIPTION

Figure 1:
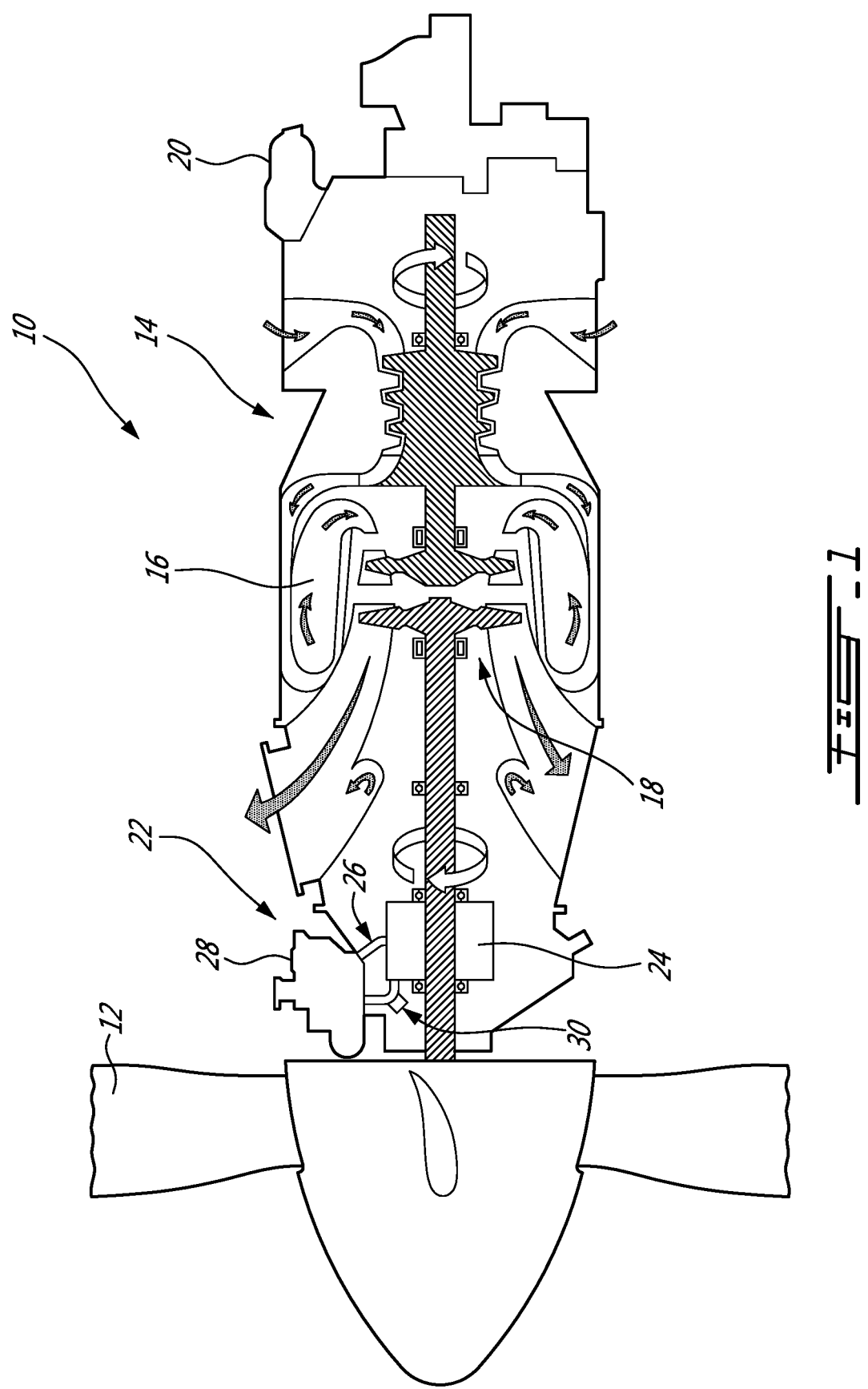
FIG. 1 is a schematic cross-sectional view of a gas turbine engine.

FIG. 1 illustrates a gas turbine engine 10 of a type preferably provided for use in subsonic flight, generally comprising in serial flow communication a propeller 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. The engine 10 further includes an engine controller 20 for controlling flight parameters of the gas turbine engine 10. The flight parameters may be, for instance, fuel flow regulation, thrust management, and actuation of valves and pumps required for proper operation of the engine 10.

The engine 10 further includes a lubrication system 22 operatively connected to a rotating component 24, which may be, for instance, a gearbox 24 of the engine 10. The lubrication system 22 includes a fluid circuitry 26 circulating a lubricant in and out of the gearbox 24. In the embodiment shown, a pump 28 is used for circulating the lubricant within the fluid circuitry 26.

The engine 10 includes a lubricant debris monitoring system 30 operatively connected to the lubrication system 22. The lubricant debris monitoring system 30 may be connected for example to the fluid circuitry 26 of the lubrication system 22. The lubricant debris monitoring system 30 may be configured for collecting debris within the lubricant and for collecting data about a level of debris within the lubricant.

Figure 2:
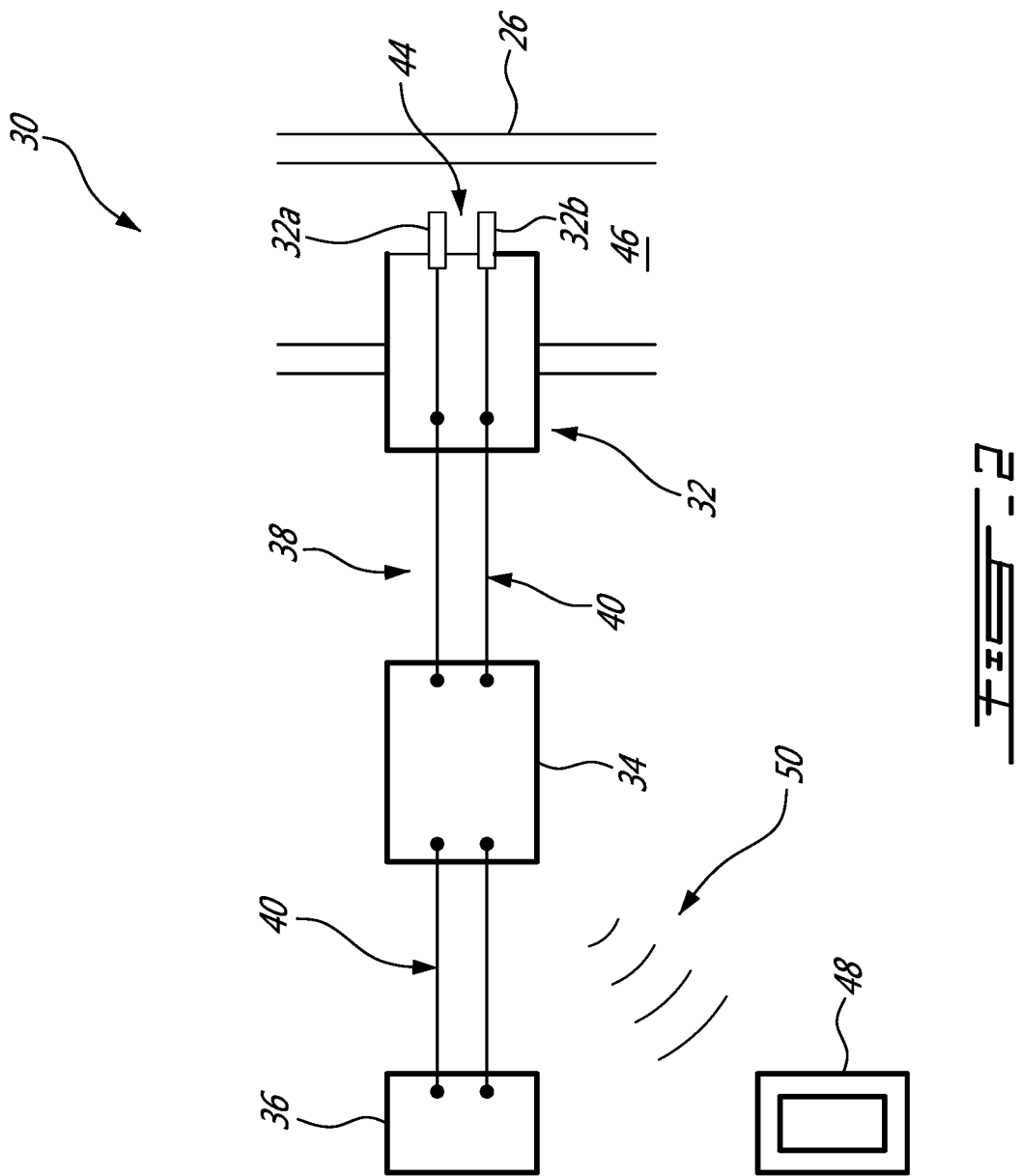
FIG. 2 is a schematic symbolic view of a lubricant debris monitoring system for a gas turbine engine such as that of FIG. 1.
Figure 3:
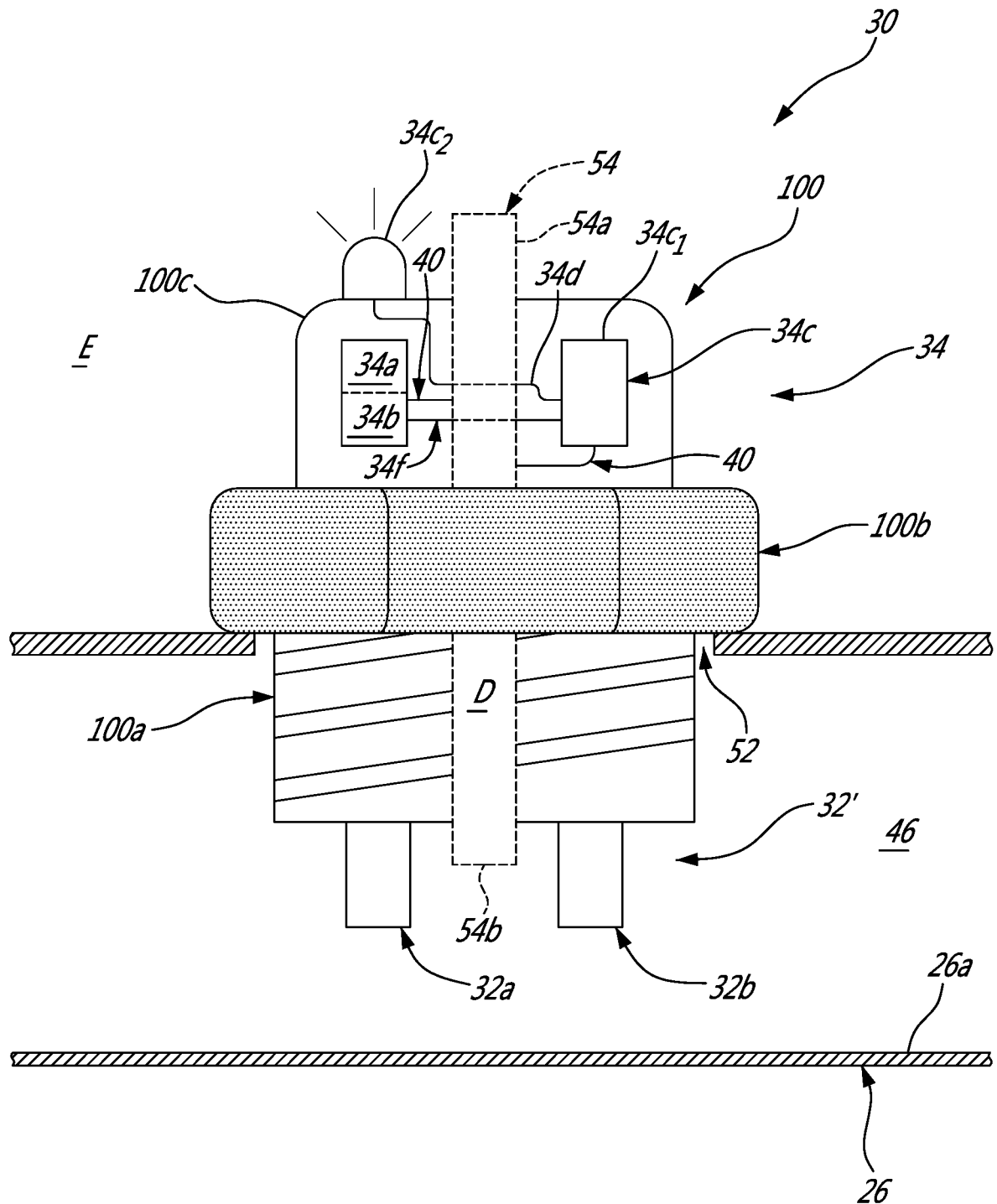
FIG. 3 is a schematic view of the lubricant debris monitoring system of FIG. 2.

Referring now to FIGS. 2 and 3, a schematic view of the lubricant debris monitoring system 30 in accordance with one embodiment is illustrated. The lubricant debris monitoring system 30 includes a sensor 32 configured for being exposed to the lubricant and for detecting debris within the lubricant, and a data module 34 operatively connected to the sensor 32. A power source 36 is used for powering the sensor 32 and the data module 34. The power source 36 may be either dedicated to the lubricant debris monitoring system 30 or be an external power source such as a generator of the gas turbine engine 10 or an electrical system of an aircraft. In the embodiment shown, an electric circuit 38 electrically connects by wires 40 the power source 36 to the sensor 32 and to the data module 34 via methods known in the art.

In the embodiment shown, the sensor 32 has two electrodes 32a, 32b that are spaced apart from each other by a gap 44. The gap 44 is configured to be filled with the lubricant. The two electrodes 32a, 32b are suitably electrically connected to the electric circuit 38 and bathe in the lubricant. For example, the electrodes 32a, 32b extend through a flow path 46 of the lubricant within the fluid circuitry 26 of the lubrication system 22. In another embodiment, the electrodes 32a, 32b are in a reservoir of the lubrication system 22. The two electrodes 32a, 32b are submerged in the lubricant (e.g., within the flow path 46) and are used to determine the presence of debris therein. More details about this aspect are presented herein below.

In the embodiment shown, the lubricant debris monitoring system 30 is independent from the engine 10, i.e., it is a self-contained system. The data module 34 is configured to transmit the data regarding the level of debris to a third party 48 without interference with the engine controller 20 (FIG. 1), i.e., without the engine controller 20 being a compulsory intermediate. A communication link 50 is established between the data module 34 and the third party 48. The communication link 50 bypasses the engine controller 20. Stated otherwise, the lubricant debris monitoring system 30 does not require the engine controller 20, or any other system of the aircraft equipped with the engine 10, for communicating and transferring its data to the third party 48. The engine controller 20 may wirelessly communicate with a cockpit of the aircraft equipped with the engine 10. In such a case, a communication link established between the engine controller 20 and the cockpit is parallel to, and separate from, the communication link 50 between the lubricant debris monitoring system 30 and the third party 48. In the embodiment shown, the third party 48 is a smartphone, a PDA, or any other suitable device. The communication link 50 may in an embodiment be bi-lateral.

The lubricant debris monitoring system 30 as discussed above can be achieved with the exemplary features illustrated in FIG. 3. According to the illustrated embodiment, the sensor 32, the data module 34, and the power source 36 are mounted on a common device, such as plug 100. In a particular embodiment, the plug 100 is totally independent from the engine 10 as it is self-powered. Hence, the plug 100 may be a self-contained device for the detection of debris within the lubricant. This aspect is described herein below.

In the embodiment shown, the plug includes a threaded portion 100a configured for engaging a corresponding threaded aperture 52 defined through a wall 26a of the lubrication system 22. By inserting the threaded portion 100a in the threaded aperture 52, the two electrodes 32a, 32b extend into the lubricant and are in contact with the lubricant. The plug 100 may or may not include a tool receiving portion 100b configured for being engaged by a wrench for screwing the plug 100 within the corresponding threaded aperture 52. As shown, the tool receiving portion 100b has a shape of an hexagonal nut. The data module 34 may be located within or mounted to an external portion 100c of the plug 100 that is configured to remain exposed to air of an environment E outside the flow path 46.

For being autonomous, the power source 36 may be an energy harvesting device D such as, in the embodiment shown, a thermoelectric generator 54. The thermoelectric generator 54 includes a cold probe 54a and a hot probe 54b. The hot probe 54b extends through the threaded portion 100a of the plug 100 such that it extends into the lubricant to be in contact therewith whereas the cold probe 54a extends through the external portion 100c such that is it exposed to the environment E outside of the flow path 46 to be in contact with air of the environment E. The thermoelectric generator 54 is configured to generate electricity from a temperature difference between the lubricant and air of the environment E outside the lubrication system 22. Any suitable thermoelectric generator 54 known in the art may be used. A battery may be required to store energy generated by the thermoelectric generator 54. Alternately, the power source 36 may be a battery, or may be a connection to an electrical system of the gas turbine engine 10 or of the aircraft. In a particular embodiment, by generating its own power, the lubricant debris monitoring system 30 is totally autonomous from the engine 10. The energy harvesting device D is configured for powering all functions of the data module 34. The latter includes components for data acquisition. Alternately, photoelectric cells (e.g., solar cell) may be used to power the debris monitoring system 30. The photoelectric cells may be affixed to an exterior of the engine 10 to be exposed to solar radiation. A battery may be used for storing the energy from the cell.

In the embodiment shown, the data module 34 includes a computer readable medium 34a and a processor 34b communicatively connected to the computer readable medium 34a. Any suitable processor and computer readable medium may be used. The computer readable medium may be a computer readable memory having recorded thereon statements and instructions for execution by the processor, in accordance with the method described below. The computer readable medium 34a is configured for storing the data regarding the level of debris in the lubricant. The processor 34b is configured for interpreting signals from the sensor 32 and for writing the data on the computer readable medium 34a.

In the embodiment shown, the sensor 32 may further include a magnetic chip collector 32' generating a magnetic field for attracting the debris. In the embodiment shown, at least one of the two electrodes 32a, 32b is magnetic for attracting the debris. In the embodiment shown, when an amount of debris collected by the magnetic chip collector 32' via the magnetic electrode 32a is below a given threshold, the electric circuit 38 (FIG. 2) is opened between the two electrodes 32a, 32b such that no electrical communication is possible between the two electrodes 32a, 32b via the gap 44. With time, the magnetic electrode 32a cumulates debris thereon such that the gap 44 between the two electrodes 32a, 32b is gradually bridged by debris. The given threshold may correspond to an amount of debris required to bridge the gap 44. When the gap 44 is bridged, the electric circuit 38 becomes closed and current may circulate from one of the two electrodes 32a, 32b to the other via the bridged gap 44. The data module 34 via its processor 34b, which is operatively connected to the electrodes 32a, 32b and to the power source 36, is configured for performing an analysis of an electrical signal between the electrodes 32a, 32b and for storing occurrences of at least one characteristic of the electrical signal exceeding a respective threshold. The analysis may be stored on the computer readable medium or elsewhere (e.g., cloud).

More specifically, a quantity of the debris within the gap 44 varies an electrical resistance between the electrodes 32a, 32b. As the current varies inversely to the electrical resistance, by varying the quantity of the debris bridging the gap 44 the electrical resistance between the electrodes 32a, 32b varies and a magnitude of the current between the electrodes varies.

Therefore, the characteristics of the electrical signal may be a magnitude of a current between the electrodes, a duration of a period during which the magnitude of the current remains beyond a current threshold, and/or a frequency of occurrences where the magnitude of the current exceeds the current threshold. For the duration of the period, the threshold is a duration threshold expressed in a unit of time. For the frequency of occurrences, the threshold is a frequency threshold expressed in a number of occurrences over a unit of time (e.g., number of occurrences per minute).

In the embodiment shown, the lubricant debris monitoring system 30 allows continuous monitoring of the electric signal between the electrodes 32a, 32b and thus of a level of debris captured by the magnetic chip collector 32.

The data/analysis stored on the computer readable medium 34a is accessible to the third party 48 for inspection by a user. In the embodiment shown, this accessibility of the data regarding the analysis to the third party 48 is provided by a communication system 34c of the data module 34. The communication system is communicatively connected to the processor 34b and configured for transmitting the analysis of the electrical signal. The communication system 34c may be a receiver/transmitter for secure bidirectional communication with the third party 48, so as to accept commands from the third party 48 (e.g., reset, uploads, etc). In contrast, the communication system 34c may be limited to uni-directional communication with the engine controller 20, for example to inform an operator of excess debris in the lubricant, and the requirement for maintenance. The communication standards may for instance be Bluetooth® or wifi. The communication system 34c may be communicatively separated from the engine controller 20. As illustrated, the communication system 34c includes electronic components $34c_1$ operatively connected to a wireless antenna $34c_2$ by suitable means such as wires 34d. The communication system 34c is communicatively connected to the processor 34b by wires 34f for transferring the data from the computer readable medium 34a to the electronic components $34c_1$ of the communication system 34c and hence to the third party 48 via the wireless antenna $34c_2$.

In the embodiment shown, the lubricant debris monitoring system 30 allows the detection of transient chips. Transient chips are debris that momentarily get trapped by a magnetic field of the magnetic electrode 32a so that they bridge the gap 44 between the two electrodes 32a, 32b of the magnetic chip collector 32', thereby closing the circuit 38, but that do not remain attached to the collector 32'. The transient chips may be dislodged by, for instance, the flow of lubricant circulating in the flow path 46 around the transient chips. The transient chips, which are momentarily trapped by the magnetic field, induce fluctuations of at least one of the characteristics of the signal that are discussed herein above. Stated otherwise, the transient chips may cause the magnitude of the current between the two electrodes to exceed the current threshold during a certain period of time. Stated otherwise, a transient chip may decrease an electrical resistance between the electrodes 32a, 32b and allow circulation of a current that is greater in magnitude than that of a current passing between the electrodes without the transient chip.

In the embodiment shown, the processor 34b may write on the computer readable medium 34a that, at some point, the gap 44 was bridged. In a particular embodiment, this is advantageous as it allows a user to notice that, although the gap 44 might not be bridged at the time of inspection, the gap 44 was bridged at some point. Hence, this might offer advanced warning that the gap 44 is close to be bridged. This might offer an earlier notification regarding components deterioration (e.g., the gearbox 24) compared to an existing chip collector that simply collects the chip and requires a visual inspection to determine the level of debris within the lubricant.

Previous collectors require a maintenance technician to open cowls of the engine 10 to access a magnetic chip collector periodically at intervals, such as from six to twelve months, or every fifty hours of flight. Such a procedure may be expensive and time consuming. Moreover, installing a device to actively monitor the level of debris within the lubricant typically requires wirings to connect the device to a cockpit annunciator. This is a cumbersome task and adds weight to the aircraft. In some cases, such a modification is not possible for all engines.

In a particular embodiment, the above described features of the lubricant debris monitoring system 30 allows its installation in an engine that has not been initially configured for actively monitoring its lubrication system 22. Hence, in a particular embodiment, installation of the lubricant debris monitoring system 30 does not require any wire, any modification of the cockpit, and does not require electricity from the engine 10 or aircraft.

In a particular embodiment, by being self-contained, the lubricant debris monitoring system 30 allows the pilot or the maintenance technician to monitor the lubrication system 22 for presence of magnetic particles on demand using the third party 48 (FIG. 2) (e.g., PDA device, smartphone application). Hence, the lubricant debris monitoring system 30, which might enhance safety and reduce engine repair costs, might be available to operators of all turbine powered aircraft. In such a case, the data module 34 may provide its identity to the third party 40, for identification of the aircraft. In a particular embodiment, the lubricant debris monitoring system 30 might be used for retrofitting aircraft/engines that do not have debris monitoring capabilities. Moreover, the periodic maintenances might not be required.

In a particular embodiment, the sensor 32 is configured for monitoring a magnitude of an electric conductivity of the lubricant between its two electrodes 32a, 32b via the gap 44. The electric conductivity of the lubricant might be altered by the presence of the debris therein. For instance, the electric conductivity might increase if the electric conductivity of the debris is greater than that of the lubricant free of debris. In this particular embodiment, the lubricant debris monitoring system 30 is configured for continuously monitoring the electric conductivity of the lubricant. For example, the system 30 might be configured for measuring the conductivity at regular time intervals and storing the measured conductivity within the computer readable medium 34a. The user (e.g., pilot, maintenance technician), via the third party 48, may then review the data that would represent an evolution in time of the conductivity of the lubricant. The lubricant debris monitoring system 30 might be configured for sending a notification to the third party 48 when the conductivity reaches a predetermined threshold that is indicative of component deterioration. The system 30 might be configured to measure a resistance encountered by a current circulating between two electrodes that varies with the presence of the debris in the lubricant. In a particular embodiment, the sensor 32 is configurable to set the predetermined threshold of the resistance or of the conductivity.

In a particular embodiment, the debris monitoring system 30 may be configured to measure a temperature and a pressure of the lubricant within the lubrication system 22.

This might be achieved by incorporating a thermocouple and/or a piezoelectric transducer in the system 30. The system 30 may hence be configured for storing and analysing data regarding the pressure and/or the temperature of the lubricant. This might allow for the detection of a deterioration in the seals that control ingress of air in to the lubrication system 22.

In a particular embodiment, the sensor 32 may include a sensor coil wrapped around a conduit of the lubrication system 22 circulating the lubricant. The sensor coil is configured for receiving a current generating a magnetic field attracting the debris. The sensor 32 may be configured for measuring variations of the magnetic field as the result of the passage of the debris within the conduit. In such a case, the sensor measures a variation with time of the magnetic field which may offer information regarding the level of debris within the lubricant. In this particular embodiment, data about the size of the debris may also be measured. These data may be derived from an amplitude and/or a phase of an output signal from the sensor coil.

Referring to FIGS. 1-3, for operating the lubricant debris monitoring system 30, the debris circulating within the lubricant of the lubrication system 22 are attracted toward the electrodes 32a, 32b of the magnetic chip collector 32'. The electrical signal between the electrodes 32a, 32b is analyzed. The electric signal is affected by the debris located within the gap 44 between the electrodes 32a, 32b. Occurrences of at least one of the characteristics of the electrical signal exceeding a respective threshold are stored. The analysis of the electrical signal is then transmitted. The analysis may be wirelessly transmitted and may be transmitted by establishing the communication link from the debris monitoring system 30. In the embodiment shown, the communication link bypasses the engine controller 20 of the gas turbine engine 10.

As illustrated, storing the occurrences of the characteristic includes storing the occurrences of at least one of a magnitude of a current between the electrodes exceeding a current threshold, a duration of a period during which the magnitude of the current remains beyond the current threshold exceeding a duration threshold, and a frequency of occurrences where the magnitude of the current exceeds the current threshold exceeding a frequency threshold.

In the embodiment shown, the lubricant debris monitoring system 30 further alerts a user (e.g., maintenance crew, pilot) that an impending maintenance action of the gas turbine engine is required when at least one of the characteristics of the signal exceeds its respective threshold. As aforementioned, the transient chips within the lubricant cause the characteristics of the signal to vary. When too much transient chips are present within the lubricant, the user may be notified that maintenance of the gas turbine engine is required because the presence of these chips might be caused by components deterioration and might be indicative of an impending failure of said components. In the embodiment shown, power for powering the lubricant debris monitoring system 30 is generated. As shown, the power is generated by converting in electricity a temperature difference between the lubricant and air of the environment E outside the lubricant.

The above description is meant to be exemplary only, and one skilled in the art will recognize that changes may be made to the embodiments described without departing from the scope of the invention disclosed. For instance, it is understood that the disclosed system may be used to monitor lubricant of other types of engines (e.g., piston engines, steam turbines) and/or of other components (e.g., gearboxes). Still other modifications which fall within the scope of the present invention will be apparent to those skilled in the art, in light of a review of this disclosure, and such modifications are intended to fall within the appended claims.

The invention claimed is:

1. A lubricant debris monitoring system for a gas turbine engine, comprising:
   a magnetic chip collector operatively coupled to a lubrication system, the magnetic chip collector having electrodes defining a gap therebetween, the gap exposed to lubricant of the lubrication system, the magnetic chip collector in use generating a magnetic field for attracting the debris toward the electrodes, the magnetic chip collector configured to generate a signal when a metal chip in the lubricant bridges the gap and allows connection of the electrodes;
   a processor operatively connected to the electrodes of the magnetic chip collector and connected to a power source, the processor configured for performing an analysis of the signal for detecting occurrences of at least one characteristic of the signal exceeding a respective threshold and for storing the analysis with the occurrences, transient chips momentarily trapped by the magnetic field inducing fluctuations of the at least one characteristic of the signal, the at least one characteristic of the signal being one or more of a magnitude of a current between the electrodes, a duration of a period during which the magnitude of the current remains beyond a current threshold, and a frequency of occurrences where the magnitude of the current exceeds the current threshold; and
   a communication system communicatively connected to the processor and configured for transmitting the analysis of the signal.

2. The lubricant debris monitoring system of claim 1, wherein the system comprises the power source, and wherein the power source is an energy harvesting device.

3. The lubricant debris monitoring system of claim 2, wherein the energy harvesting device is a thermoelectric generator including two probes, one of the two probes configured to be in contact with the lubricant, the other of the two probes configured to be in contact with air of an environment outside the lubrication system, the thermoelectric generator configured for converting in electricity a temperature difference between the lubricant and the air of the environment.

4. The lubricant debris monitoring system of claim 1, wherein the system is provided in a form of a plug having mounted thereon the magnetic chip collector, the processor, and the communication system.

5. The lubricant debris monitoring system of claim 4, wherein the plug has a threaded portion configured for engaging a threaded aperture extending through a wall of the lubrication system.

6. The lubricant debris monitoring system of claim 1, wherein the communication system is configured to be separated from an engine controller of the gas turbine engine, the engine controller configured for controlling an operation of the gas turbine engine, the communication system transmitting the analysis via a communication link that bypasses the engine controller.

7. The lubricant debris monitoring system of claim 1, wherein the magnetic field is created by one or both of the electrodes.

8. A gas turbine engine comprising a lubrication system for lubricating rotating components of the gas turbine engine, the lubrication system having a fluid circuitry operatively connected to the rotating components and configured for circulating a lubricant; the gas turbine engine further having a lubricant debris monitoring system operatively coupled to the lubrication system, the lubricant debris monitoring system having a magnetic chip collector coupled to the lubrication system and having electrodes defining a gap therebetween, the gap exposed to the lubricant, the magnetic chip collector in use generating a magnetic field for attracting the debris toward the electrodes, the magnetic chip collector configured to generate a signal when a metal chip in the lubricant bridges the gap and allows connection of the electrodes; a processor operatively connected to the electrodes and to a thermoelectric generator including two probes, one of the two probes in contact with the lubricant, the other of the two probes in contact with air of an environment outside the lubrication system, the thermoelectric generator configured for converting in electricity a temperature difference between the lubricant and the air of the environment, the processor configured for performing an analysis of a signal between the electrodes for detecting occurrences of at least one characteristic of the signal exceeding a respective threshold and for storing the analysis with the occurrences; and a communication system communicatively connected to the processor and configured for transmitting the analysis of the signal.

9. The gas turbine engine of claim 8, wherein the magnetic field is created by one or both of the electrodes.

10. The gas turbine engine of claim 8, wherein the lubricant debris monitoring system is provided in a form of a plug having mounted thereon the magnetic chip collector, the processor, and the communication system.

11. The gas turbine engine of claim 10, wherein the plug has a threaded portion configured for engaging a threaded aperture extending through a wall of the lubrication system.

12. The gas turbine engine of claim 8, further including an engine controller for controlling an operation of the gas turbine engine, the communication system separated from the engine controller, the communication system transmitting the analysis via a communication link that bypasses the engine controller.

13. The gas turbine engine of claim 8, wherein transient chips momentarily trapped by the magnetic field induce fluctuations of the at least one characteristic of the signal, the at least one characteristic of the signal is at least one of an amplitude of the signal, a duration of a period during which the amplitude of the signal remains beyond an amplitude threshold, and a frequency of occurrences where the amplitude of the signal exceeds the amplitude threshold.

14. A method of operating a lubricant debris monitoring system of a gas turbine engine, comprising:
attracting debris circulating within a lubricant of a lubrication system toward electrodes of a magnetic chip detector, a signal between the electrodes being affected by the debris located within a gap between the electrodes, transient chips momentarily trapped within the gap inducing fluctuations of at least one characteristic of the signal;
performing an analysis of the signal between the electrodes to detect occurrences of the at least one characteristic of the signal exceeding a respective threshold, the at least one characteristic being one or more of a magnitude of a current between the electrodes exceeding a current threshold, a duration of a period during which the magnitude of the current remains beyond the current threshold exceeding a duration threshold, and a frequency of occurrences where the magnitude of the current exceeds the current threshold exceeding a frequency threshold;
storing the analysis with the occurrences; and
transmitting the analysis of the signal.

15. The method of claim 14, wherein the attracting of the debris includes attracting the debris with a magnetic filed generated by one or both of the electrodes.

16. The method of claim 14, further comprising alerting a user that an impending maintenance action of the gas turbine engine is required when the at least one characteristic of the signal exceeds the respective threshold.

17. The method of claim 16, wherein generating the power comprises converting in electricity a temperature difference between the lubricant and air of an environment outside the lubrication system.

18. The method of claim 14, wherein transmitting the analysis includes transmitting the analysis via a wireless communication link.

19. The method of claim 14, wherein transmitting the analysis of the signal includes establishing a communication link from the debris monitoring system, the communication link bypassing an engine controller of the gas turbine engine configured for controlling an operation of the gas turbine engine.

* * * * *